United States Patent
Hahn et al.

(10) Patent No.: US 7,683,214 B2
(45) Date of Patent: Mar. 23, 2010

(54) METHOD OF PRODUCING BENZOPHENONEIMINES

(75) Inventors: Thilo Hahn, Kirchheimbolanden (DE); Frank Haese, Dietzenbach (DE); Ulrich Köhler, Mannheim (DE); Ekkehard Schwab, Neustadt (DE); Johann-Peter Melder, Böhl-Iggelheim (DE); Jan Eberhardt, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/282,277

(22) PCT Filed: Mar. 1, 2007

(86) PCT No.: PCT/EP2007/051931
§ 371 (c)(1),
(2), (4) Date: Sep. 9, 2008

(87) PCT Pub. No.: WO2007/104650
PCT Pub. Date: Sep. 20, 2007

(65) Prior Publication Data
US 2009/0093654 A1  Apr. 9, 2009

(30) Foreign Application Priority Data
Mar. 10, 2006  (EP) .................. 06110980

(51) Int. Cl.
*C07C 249/02* (2006.01)
(52) U.S. Cl. ..................... 564/269
(58) Field of Classification Search .......... 564/269
See application file for complete search history.

(56) References Cited

U.S. PATENT DOCUMENTS

| 4,083,869 A * | 4/1978 | Isshiki et al. ............ 564/269 |
| 4,388,288 A | 6/1983 | Dupin et al. |
| 5,679,855 A | 10/1997 | Voit et al. |
| 5,684,201 A | 11/1997 | Rieber et al. |

FOREIGN PATENT DOCUMENTS

EP  0688764 A1  12/1995
EP  0713861 A1  5/1996

OTHER PUBLICATIONS

"Phenolic Resins to Pigments, Inorganic", Ullman's Encyclopedia of Industrial Chemistry, 2000, vol. 26, pp. 581-723.
Linak, E., et al., "Titanium Dioxide", CEH Marketing Research Report, 2005, pp. 1-28.
Buxbaum, G., et al., "Industrial Inorganic Pigments", Weinheim, 2005, Chapter 2.1.3.4, pp. 67-69.
"Preparation of Solid Catalysts", Handbook of Heterogeneous Catalysis, 1997, vol. 1, pp. 98-99.
Charles, G., "Sur Les Tendances Actuelles Des Sciences Chimiques ", Bulletin de la Société Chimique de France, 1963, pp. 1576-1583.
* cited by examiner

*Primary Examiner*—Brian J Davis
(74) *Attorney, Agent, or Firm*—Connolly Bove Lodge & Hutz LLP

(57) ABSTRACT

A process for the preparation of benzophenonimine (BPI) of the general formula I

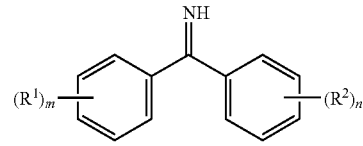

where $R^1$ and $R^2$ are $C_1$- to $C_4$-alkoxy, $C_1$- to $C_2$-alkylamine and $C_2$- to $C_4$-dialkylamine and m and n are integers from 0 to 5 and $R^1$ and $R^2$, independently of one another, may be identical or different, by reacting benzophenone (BP) of the general formula II

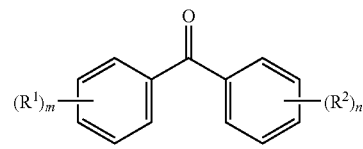

where R1, R2, m and n have the abovementioned meanings, in ammonia and in the presence of titanium dioxide, the titanium dioxide being present substantially in the anatase modification.

7 Claims, No Drawings

METHOD OF PRODUCING BENZOPHENONEIMINES

RELATED APPLICATIONS

This application is a national stage application (under 35 U.S.C. §371) of PCT/EP2007/05193 1, filed Mar. 1, 2007, which claims benefit of European Application No. 06110980.7, filed Mar. 10, 2006.

The present invention relates to a process for the preparation of benzophenonimine (BPI) of the general formula I

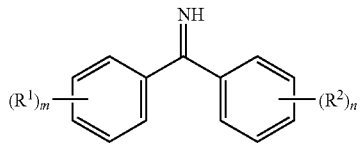

where $R^1$ and $R^2$ are $C_1$- to $C_4$-alkoxy, $C_1$- to $C_2$-alkylamine and $C_2$- to $C_4$-dialkylamine and m and n are integers from 0 to 5 and $R^1$ and $R^2$, independently of one another, may be identical or different, by reacting benzophenone (BP) of the general formula II

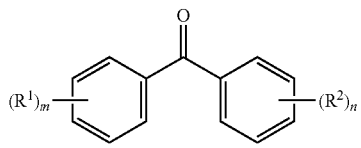

where $R^1$, $R^2$, m and n have the abovementioned meanings, in ammonia and in the presence of titanium dioxide, the titanium dioxide being present substantially in the anatase modification.

Further embodiments of the invention are described in the claims, the description and the examples. Of course, the abovementioned features and those features of the subject matter according to the invention which are still to be explained below can be used not only in the combination stated in each case but also in other combinations without departing from the scope of the invention.

In EP-A-0 713 861, benzophenone is reacted in liquid ammonia in the presence of oxides of the series of elements or mixtures thereof inter alia titanium, at temperatures of from 80 to 140° C. and pressures of from 150 to 250 bar. The patent states that the catalysts can be used in the form of powders (stirred autoclave) or in the form of tablets or extrudates (tubular reactors). As is evident from the examples, benzophenone conversions of from 91 to 98% and selectivities of 99% could be achieved in a continuous tubular reactor with the use of titanium oxides, but the benzophenone conversion decreases with increasing loading under identical reaction conditions.

By means of the present invention, it was intended to develop an improved process for the preparation of benzophenonimines. The process according to the invention permits high conversions of benzophenones with good selectivities. In a continuous preparation, the loading of the catalyst with starting material (benzophenone) can be increased compared with conventional processes without reducing the conversion of benzophenones and without adversely affecting the selectivity. This permits, for example, an increase in the capacity of existing plants and a reduction of the reaction volume in the case of new plants and an associated reduction of the total capital costs.

Accordingly, a process for the preparation of benzophenonimine (BPI) of the general formula I

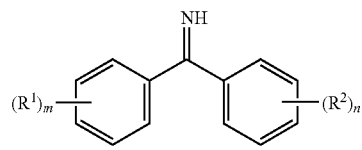

where $R^1$ and $R^2$ are $C_1$- to $C_4$-alkoxy, $C_2$- to $C_2$-alkylamine and $C_2$- to $C_4$-dialkylamine and m and n are integers from 0 to 5 and $R^1$ and $R^2$, independently of one another, may be identical or different, by reacting benzophenone (BP) of the general formula II

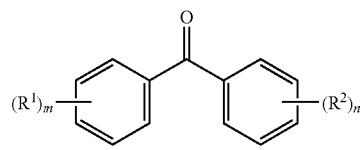

where $R^1$, $R^2$, m and n have the abovementioned meanings, in ammonia and in the presence of titanium dioxide, the titanium dioxide being present substantially in the anatase modification, was found.

Titanium dioxide may be present in three modifications: rutile, anatase and brookite. The modification is defined as the crystal structure in which titanium dioxide crystallizes. Rutile and anatase crystallize with a tetragonal lattice while brookite has an orthorhombic crystal system.

The crystal structure of titanium dioxide can be determined analytically by means of X-ray diffractometry. An exact working method for determining the proportion of anatase in titanium dioxide is mentioned in the standard ASTM D 3720.

Processes for the preparation of titanium dioxide are described in the literature [cf. in this context Ullmann's Encyclopedia of Industrial Chemistry, 6th Edition, 2000 Electronic Release, chapter "Pigments inorganic"; CEH Marketing Research Report, "Titanium Dioxide", 2005; Industrial Inorganic Pigments, edt. by G. Buxbaum and G. Pfaff, Wiley VCH, Weinheim 2005]. Commercial processes for the preparation of titanium dioxide are the sulfate process and the chloride process. Both from the sulfate process and from the chloride process, titanium dioxide can be obtained both in the rutile modification and in the anatase modification, it being possible to obtain titanium dioxide which is present substantially in the anatase modification preferably from the sulfate process. After preparation is complete, titanium dioxide can be modified by an aftertreatment step. Suitable aftertreatment steps are described in section 2.1.3.4 of "Industrial Inorganic Pigments", edt. by G. Buxbaum and G. Pfaff, Wiley VCH, Weinheim 2005.

Titanium dioxide is commercially available in various modifications. Titanium dioxides which are to be assigned to type A (anatase type) and group A1 according to EN ISO 591-1:2000 are particularly suitable.

The titanium dioxide used in the process according to the invention is present substantially in the anatase modification. The titanium dioxide used can, however, also be present exclusively in the anatase modification. However, it is also possible for the titanium dioxide to be present not completely in the anatase modification but to have proportions of other modifications, in particular rutile. Preferably, the titanium dioxide used in the process according to the invention is present to an extent of at least 50% by weight in the anatase modification, advantageously to an extent of at least 80% by weight in the anatase modification and particularly advantageously to an extent of at least 95% by weight in the anatase modification, based on the titanium dioxide used altogether.

The process according to the invention can be operated batchwise or continuously.

The titanium dioxide can be used as powder or in the form of moldings, such as extrudates, tablets, or granules.

In the batchwise process, titanium dioxide is preferably used as powder. The ratio of titanium dioxide powder to benzophenone of the formula II is in general in the range of from 0.001 to 5 kg of titanium dioxide/kg of BP, preferably in the range of from 0.01 to 3 kg of titanium dioxide/kg of BP and particularly preferably in the range of from 0.5 to 2 kg of titanium dioxide/kg of BP.

In the continuous process, titanium dioxide is preferably used as moldings. The processing of titanium dioxide to give moldings is designated below as formulation. Titanium dioxide can be formulated by means of different methods. The formulation of titanium dioxide to give catalyst moldings can be effected, for example, by processes known per se for the preparation of catalyst moldings, as described, for example, in Ertl, Knözinger, Weitkamp: "Handbook of Heterogeneous Catalysis", VCH Weinheim, 1997, page 98 et seq. The formulation of catalyst moldings from titanium dioxide is also disclosed, for example, in U.S. Pat. No. 4,388,288. According to the abovementioned documents, the formulation usually comprises the process steps of compounding (mixing), of shaping and of drying or calcination.

As is also evident from the reference mentioned, processing assistants, such as binders, pore formers and pasting agents and water can be added to the titanium dioxide during the compounding.

The proportion of titanium dioxide in the catalyst molding can as a rule be chosen so that, after the drying and/or calcination described below, the titanium content of the catalyst molding is at least 15% by weight, preferably at least 30% by weight and particularly preferably at least 50% by weight, based in each case on the total mass of the catalyst molding. The maximum titanium content of a catalyst molding comprising pure titanium dioxide is 59.95% by weight.

By the process of shaping which is likewise described in said references (Ertl, Knözinger, Weitkamp. "Handbook of heterogeneous catalysis", VCH Weinheim, 19971, page 98 et seq., U.S. Pat. No. 4,388,288), it is possible to obtain moldings in any three-dimensional shape, e.g. round, polygonal, elongated or the like, for example in the form of extrudates, tablets, granules, spheres, cylinders or grains. Customary processes for shaping are, for example, extrusion, tabletting, i.e. mechanical compression or pelletizing, i.e. compacting by circular and/or rotational movements.

The lower limit of the molding size is chosen so that the pressure buildup caused by the flow resistance owing to the increased density of solids in the reactor remains technically controllable and the moldings still have sufficient mechanical stability. The size of the titanium dioxide moldings obtained by the shaping process should preferably be from 0.5 to not more than 10 mm, particularly preferably from 1 to 5 mm, after the drying and/or calcination step described below.

The shaping process is as a rule followed by a drying and/or calcination step in which the molding is usually heated at relatively high temperatures. During the drying and/or calcination step, it should be noted that the monotropic transformation of anatase into rutile takes place at a reaction temperature of more than 700° C. ("Industrial Inorganic Pigments", G. Buxbaum and G. Pfaff, Wiley-VCH, Weinheim, page 51). If desired, the ratio of anatase to rutile can be adjusted by the duration of the reaction and the reaction temperature in the calcination. In a preferred embodiment, the drying and/or calcination step is carried out at temperatures below 600° C. in order to avoid the transformation of anatase into rutile. Particularly preferably, the drying and/or calcination step is carried out at temperatures of from 200 to 600° C.

The cutting hardness after complete drying and/or calcination of moldings which were extruded in the form of extrudates may be in the range of small values, such as from 2 N to 10 N, medium values, such as greater than 10 N to 20 N, or high values, such as greater than 20 N or greater than 25 N. The cutting hardness can be determined by means of the measuring method described in the comparative example.

The BET surface area determined according to the German standard DIN 66.131 by the multipoint method by means of the volumetric process may be in the range of from 10 to 2000 $m^2/g$, preferably in the range of from 80 to 120 $m^2/g$.

A part of the titanium dioxide can be replaced by other oxides and/or mixed oxides. Suitable as such are oxides and/or mixed oxides of the elements boron, aluminum, gallium, indium, silicon, germanium, tin, lead, phosphorus, arsenic, antimony, bismuth, scandium, yttrium, zirconium, vanadium, niobium, tantalum or tungsten, preferably oxides and/or mixed oxides of the elements boron, aluminum, gallium, silicon, tin, lead, antimony, bismuth, zirconium vanadium, niobium or tungsten or particularly preferably oxides and/or mixed oxides of the elements aluminum, silicon, zirconium, vanadium or tungsten. The proportion of the abovementioned other oxides and/or mixed oxides may vary within wide ranges. It may be up to 80% by weight but is preferably 50% by weight or less, particularly preferably not more than 20% by weight, based in each case on the total mass of the oxides used, consisting of titanium dioxide and the abovementioned other oxides and/or mixed oxides.

Benzophenones and ammonia are used as starting materials in the process according to the invention.

Benzophenones of the general formula II can be used in the melt or in solution, preferably in the melt.

In the compound, m and n are integers from 0 to 5 and the substituents $R^1$ and $R^2$ in the compounds I and II have the following meanings:

$R^1$ and $R^2$ may be:
  $C_1$- to $C_4$-alkoxy, such as methoxy, ethoxy, n-propoxy, isopropoxy, n-butoxy, isobutoxy, sec-butoxy or tert-butoxy, preferably methoxy, ethoxy, n-propoxy, or n-butoxy, particularly preferably methoxy or ethoxy,
  $C_1$- to $C_2$-alkylamine, such as methylamine or ethylamine, preferably methylamine,
  $C_1$- to $C_4$-dialkylamine, such as dimethylamine or diethylamine, preferably dimethylamine.

$R^1$ and $R^2$, independently of one another, may be identical or different.

If an aromatic nucleus is substituted by more than one substituent $R^1$ or more than one substituent $R^2$, the substituents which are present on a nucleus may be either identical to or different from one another.

The substituents $R^1$ and $R^2$ may be substituted at any position of the aromatic nuclei; preferably, however, the substituents R¹ and R² are substituted in the ortho and/or para position. The substitution pattern can be symmetrical or asymmetrical.

A benzophenone having the CAS number 119-61-9 which has no substituents and in which m and n have a value of zero is particularly preferably used in the reaction. This benzophenone is preferably used in the melt.

Ammonia is used as a further starting material in the reaction. Ammonia can be used in liquid or supercritical form. Preferably, ammonia is used in liquid form.

As a rule, a molar excess of ammonia relative to the benzophenone of formula II is used. Preferably, the molar ratio of ammonia to benzophenone is from 10 to 100:1, preferably from 25 to 50:1 and particularly preferably from 30 to 40:1.

The process can be carried out either batchwise, preferably in a stirred autoclave, or continuously, preferably in a tubular reactor, preferably continuously in a tubular reactor.

The temperatures are in general in a range of from 50 to 150° C., preferably from 80 to 140° C., particularly preferably from 120 to 140° C. The pressures are usually in a range of from 50 to 350 bar, preferably from 150 to 250 bar, particularly preferably from 180 to 220 bar.

The catalyst space velocity set in continuous operation is as a rule chosen so that a minimum concentration of benzophenonimine in the starting stream is obtained. As a rule, the minimum concentration of benzophenonimine in the starting stream is more than 80% by weight, preferably more than 90% by weight and very particularly preferably more than 95% by weight.

The ranges stated below for typical catalyst space velocities are not to be understood as meaning strict limits for the loadability of the catalyst but as empirical values which may be influenced, for example, by the reaction conditions and the reactor geometry. The maximum catalyst space velocity can, however, easily be determined by the person skilled in the art by experiments. Under the reaction conditions mentioned as being particularly preferred, for example at space velocities of at least 0.1 kg of BP per kilogram of catalyst per hour (kg BP/(kg$_{cat}$·h)), for example from 0.2 to 3 kg of BP per kilogram of catalyst per hour (kg BP/(kg$_{cat}$·h)), preferably from 0.5 to 2.5 kg BP/(kg$_{cat}$·h) and particularly preferably from 0.7 to 2.0 kg BP/(kg$_{cat}$·h), minimum concentrations of 95% by weight of benzophenonimine can be obtained.

In the batchwise process, titanium dioxide can preferably be used as powder. The ratio of titanium dioxide powder to benzophenone in the batchwise process should be, as described above, in the range of from 0.001 to 10 kg of titanium dioxide/kg of BP, preferably in the range of from 0.01 to 3 kg of titanium dioxide/kg of BP and particularly preferably in the range of from 0.5 to 2 kg of titanium dioxide/kg of BP.

Of course, if the activity of the titanium dioxide used in the reaction declines, a regeneration, for example by washing, is possible. For example, liquids such as ammonia, water or alcohols, such as methanol, ethanol or propanol, can be used for the washing. Suitable wash liquids may also be mixtures of the abovementioned liquids.

Benzophenonimines of formula I can be used as building blocks in synthetic chemistry. In particular, a benzophenonimine which has no substituents and in which m and n assume values of zero can be used as a precursor in the preparation of light stabilizers (e.g. ethyl 2-cyano-3,3-diphenylacrylate) [Bull. Chem. Soc. Fr. (1963) 1576-1583].

An advantage of the process according to the invention is that better yields and selectivities than in conventional processes are achieved in comparison with the prior art.

A further advantage of the process according to the invention is that the loading of the catalyst with starting material can be increased in a continuous preparation in comparison with conventional processes (prior art) without a reduction in the conversion of benzophenones and without a deterioration in the selectivities. This permits, for example, an increase in the capacity of existing plants and a reduction of the reaction volume in the case of new plants and an associated reduction of the total capital costs while maintaining a defined product quality. In the present case, product quality is defined as the minimum content of benzophenonimine and the maximum content of benzophenone which are obtained after the end of the reaction or at the exit of the continuous reactor after the process according to the invention has been carried out in a batch reactor. The requirements with respect to the product quality are dependent on the further use of the benzophenonimine and the associated customer requirements.

In the experiments described below, the term benzophenonimine is used below for a benzophenonimine of the formula I which has no substituents and in which m and n have a value of zero. Furthermore, the term benzophenone is used for a benzophenone of the formula II which has no substituents and in which m and n have a value of zero (CAS number 119-61-9).

As a measure of the loadability of the catalysts, a minimum concentration of benzophenonimine of 95% in the starting stream was taken as a specification limit in the continuously operated experiments in a tubular reactor which are described below. The loading of the catalyst with benzophenone was increased in the continuous experiments until the concentration of benzophenonimine fell below the minimum concentration of 95% of benzophenonimine. The loading at which the specification with respect to the minimum concentration of benzophenonimine (95%) in the starting stream is just reached is defined as the maximum loadability in the following experiments. The contents of benzophenone and benzophenonimine and of byproducts were determined by means of gas chromatography as percentages by area (A %). Here, the percentages by area of the signals relate to the total area below the measured signals with the exception of the water signal.

The benzophenone conversion C (BP) is calculated according to the following formula:

$$C(BP) = \frac{A\ \%\ (BP)_{Start} - A\ \%\ (BP)_{End}}{A\ \%\ (BP)_{Start}}$$

The yield of benzophenonimine Y(BPI) is obtained from the percentages by area of the benzophenone signal.

$$Y(BPI) = A\%(BPI)$$

The selectivity of benzophenonimine S(BPI) is calculated as the quotient of benzophenonimine yield and benzophenone conversion:

$$S(BPI) = \frac{Y(BPI)}{C(BP)}$$

The invention is explained in the following examples.

Measurement of the Cutting Hardness:

The measurement of the cutting hardness was effected using an apparatus of the type BZ 2.5/TS1S from Zwick-Roell. The preliminary load was 0.5 N, the preliminary load speed 10 mm/min and the test speed 1.6 mm/min. The width of the blade of the knife used was 0.6 mm. The stated measured value is the mean value from testing of 30 catalyst moldings which have an extrudate shape.

EXAMPLE 1

Process According to the Invention—Continuous

A tubular reactor was filled with 500 ml of catalyst molding (extrudates) having a diameter of 1.5 mm. The titanium content was determined as a measure of the proportion of titanium dioxide in the catalyst molding. The catalyst molding consisted of pure titanium dioxide. The titanium dioxide was present in a proportion of more than 99% in the anatase modification. The reaction was carried out at a temperature of 120° C. and a pressure of 200 bar. The reactor was operated with different space velocities of from 0.3 kg BP/(kg$_{cat}$·h) and 1.2 kg BP/(kg$_{cat}$·h) (cf. table 1). The molar starting material ratio of ammonia to benzophenone was 38:1. The BET surface area, measured according to DIN 66.131, was 100 m$^2$/g. The pore volume, measured by means of mercury porosimetry according to DIN 66133, was 0.33 ml/g. The cutting hardness was 10 NM.

TABLE 1

| Space velocity [kg BP/(kg$_{cat}$·h)] | Benzophenone conversion [%] | Benzophenonimine selectivity [%] | Benzophenonimine yield [%] |
|---|---|---|---|
| 0.5 | 94.9 | 99.8 | 94.7 |
| 0.6 | 95.1 | 99.9 | 95.0 |
| 0.7 | 95.0 | 99.9 | 95.0 |
| 0.8 | 95.1 | 99.9 | 95.0 |
| 1.0 | 95.1 | 99.9 | 95.0 |
| 1.2 | 95.1 | 99.9 | 95.0 |

Example 1 shows that the maximum space velocity had not yet been reached even at a space velocity of 1.2 kg BP/(kg$_{cat}$·h). In the experiments, a higher space velocity of the catalyst was not possible owing to the one existing limitation with regard to the transport rate of the benzophenone. With the catalysts according to the invention, space velocities of substantially more than 0.6 kg BP/(kg$_{cat}$·h) can therefore be reached and, if there are no limitations with respect to apparatus, even more than 1.2 kg BP/(kg$_{cat}$·h) can be reached. In comparison, in EP-A-0 713 861, the benzophenone conversion decreased with increasing space velocity at a catalyst space velocity of only 0.6 kg BP/(kg$_{cat}$·h).

We claim:
1. A process for preparing benzophenonimine of general formula (I)

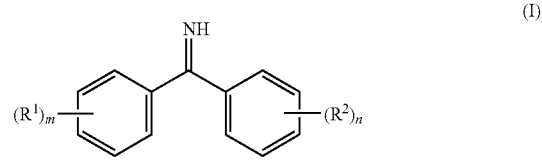

(I)

wherein
R$^1$ and R$^2$
are, identically or differently and independent of one another, C$_1$- to C$_4$-alkoxy, C$_1$- to C$_2$-alkylamine, or C$_2$- to C$_4$-dialkylamine, and
m and n
are integers from 0 to 5
comprising reacting benzophenone of general formula (II)

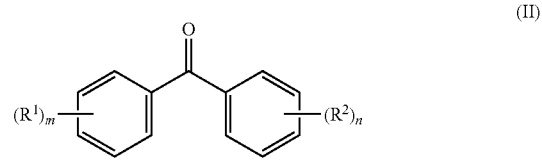

(II)

wherein R$^1$, R$^2$, m, and n are as defined above, with ammonia in the presence of titanium dioxide, wherein said titanium dioxide is present substantially in the anatase modification.

2. The process of claim 1, wherein m and n are both 0.

3. The process of claim 1, wherein a portion of said titanium dioxide is replaced by at least one oxide and/or mixed oxide from the group consisting of the elements boron, aluminum, gallium, indium, silicon, germanium, tin, lead, phosphorus, arsenic, antimony, bismuth, scandium, yttrium, zirconium, vanadium, niobium, tantalum, and tungsten.

4. The process of claim 1, wherein said titanium dioxide is in the form of moldings having a size in the range of from 0.5 mm to 10 mm.

5. The process of claim 1, wherein said process is continuous.

6. The process of claim 1, wherein said titanium dioxide is in the form of a powder.

7. The process of claim 6, wherein said process is carried out batchwise in a stirred autoclave.

* * * * *